(12) United States Patent
Govyadinov et al.

(10) Patent No.: US 10,696,939 B2
(45) Date of Patent: Jun. 30, 2020

(54) CELL LYSIS

(71) Applicant: HEWLETT-PACKARD DEVELOPMENT COMPANY, L.P., Houston, TX (US)

(72) Inventors: Alexander Govyadinov, Corvallis, OR (US); Erik D. Torniainen, Maple Grove, MN (US); David P. Markel, Albany, OR (US); Pavel Kornilovich, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/079,482

(22) PCT Filed: Apr. 22, 2016

(86) PCT No.: PCT/US2016/029017
§ 371 (c)(1),
(2) Date: Aug. 23, 2018

(87) PCT Pub. No.: WO2017/184178
PCT Pub. Date: Oct. 26, 2017

(65) Prior Publication Data
US 2019/0048309 A1     Feb. 14, 2019

(51) Int. Cl.
*B01L 3/00*     (2006.01)
*C12M 1/00*     (2006.01)
*C12N 1/06*     (2006.01)

(52) U.S. Cl.
CPC .......... *C12M 47/06* (2013.01); *B01L 3/50273* (2013.01); *B01L 3/502715* (2013.01); *B01L 3/502746* (2013.01); *C12N 1/066* (2013.01); *B01L 2300/0861* (2013.01); *B01L 2300/0864* (2013.01); *B01L 2400/0487* (2013.01); *B01L 2400/086* (2013.01)

(58) Field of Classification Search
CPC . C12M 47/06; C12M 47/00; B01L 3/502715; B01L 3/5027; B01L 3/502; B01L 3/50
USPC ............................................ 422/502, 500, 50
See application file for complete search history.

(56) References Cited

U.S. PATENT DOCUMENTS

| 5,304,487 A * | 4/1994 | Wilding | B01J 19/0093 |
| | | | 210/500.26 |
| 6,071,394 A * | 6/2000 | Cheng | B01D 57/02 |
| | | | 204/547 |
| 6,287,831 B1 * | 9/2001 | Tai | C12M 47/06 |
| | | | 204/194 |

(Continued)

OTHER PUBLICATIONS

Nan, Lang et al., "Emerging microfluidic devices for cell lysis: a review", The Royal Society of Chemistry, Lab Chip, 2014, vol. 14, pp. 1060-1073.

(Continued)

*Primary Examiner* — Christine T Mui
(74) *Attorney, Agent, or Firm* — Dierker & Kavanaugh PC

(57) ABSTRACT

In an example implementation, a method of cell lysis includes moving cell fluid from a first reservoir through a microfluidic channel toward a second reservoir, activating a lysing element multiple times as a cell from the cell fluid passes through the microfluidic channel, and moving lysate fluid that results from the activating through the microfluidic channel and into the second reservoir.

12 Claims, 6 Drawing Sheets

(56) References Cited

U.S. PATENT DOCUMENTS

| | | |
|---|---|---|
| 7,488,596 B2 | 2/2009 | Lee et al. |
| 8,263,005 B2 | 9/2012 | Laugharn et al. |
| 8,993,040 B2 | 3/2015 | Mabritto et al. |
| 9,045,757 B2 | 6/2015 | Xu et al. |
| 9,096,823 B1 | 8/2015 | Branch et al. |
| 2003/0017467 A1* | 1/2003 | Hooper ............... B01J 19/0046 435/6.11 |
| 2003/0075446 A1 | 4/2003 | Culbertson et al. |
| 2008/0305467 A1 | 12/2008 | Ussing |
| 2009/0155877 A1 | 6/2009 | Iliescu et al. |
| 2015/0184127 A1 | 7/2015 | White et al. |
| 2015/0328637 A1 | 11/2015 | Perrault et al. |

OTHER PUBLICATIONS

Hoefemann, et al., Sorting and Lysis of Single Cells by Bubblejet Technology, Sensors and Actuators B: Chemical, Jun. 20, 2012, pp. 442-445, vol. 168, Elsevier B.V.

International Search Report and Written Opinion for International Publication No. PCT/US2016/029017 dated Jan. 11, 2017, 11 pages.

Torniainen, et al., Bubble-Driven Inertial Micropump, Feb. 23, 2012, 18 pages, Hewlett-Packard Company, Imaging and Printing Division, Corvallis, Oregon, USA.

* cited by examiner

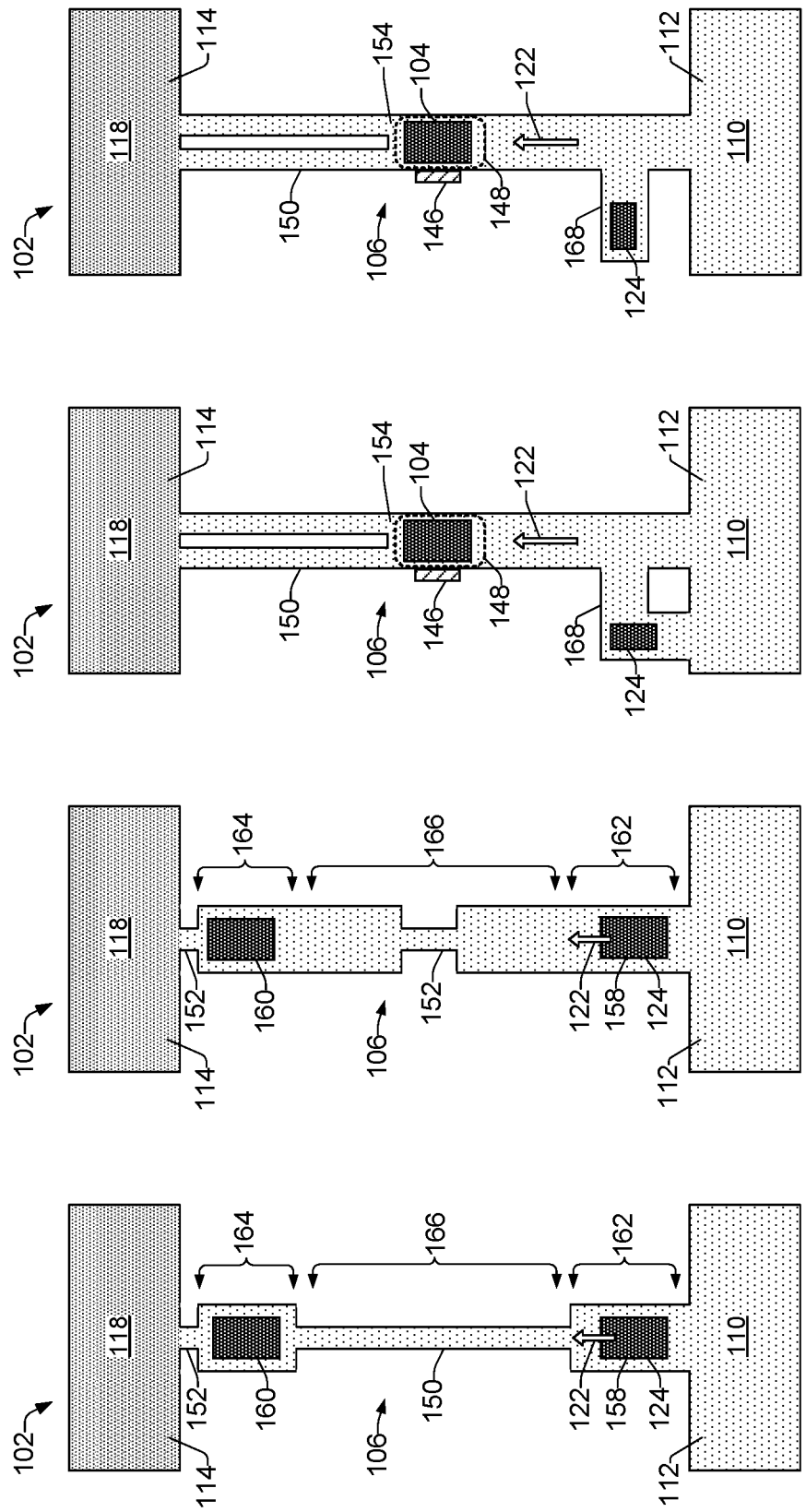

CELL LYSIS

BACKGROUND

Microfluidics has wide ranging application to numerous disciplines such as engineering, chemistry, biochemistry, biotechnology, and so on. Microfluidics can involve the manipulation and control of small volumes of fluid within various systems and devices such as inkjet printheads, lab-on-chip devices, and other types of microfluidic chip devices.

BRIEF DESCRIPTION OF THE DRAWINGS

Examples will now be described with reference to the accompanying drawings, in which:

FIGS. 10, 11, 12, 13, 14, 15a and 15b, show examples of microfluidic lysis devices that each has a fluid moving mechanism comprising a pump element disposed within a microfluidic channel;

Throughout the drawings, identical reference numbers designate similar, but not necessarily identical, elements.

DETAILED DESCRIPTION

Figure 1:
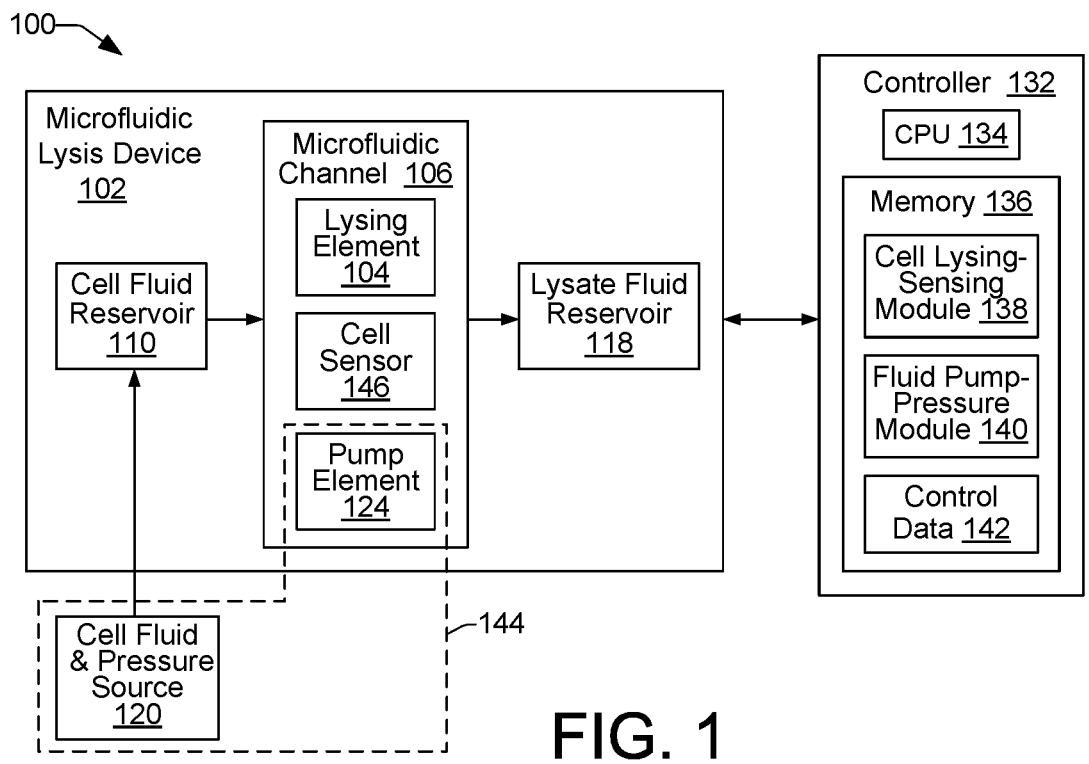
FIG. 1 shows an example of a microfluidic cell lysis system that includes a microfluidic lysis device for lysing cells.

Cell lysis is a process of extracting intracellular components for purposes such as purifying the components, retrieving DNA and RNA, and analyzing the components for genetic and/or disease characteristics. Cell lysis bursts a cell's membrane and frees the cell's inner components. The fluid containing the cell's inner components is referred to as lysate.

Cell lysis can occur naturally in various ways including viral replication within a cell that kills the cell, enzymatic dissolution of the cell's membrane, cytolysis that bursts a cell's membrane due to an osmotic imbalance that causes excess water to enter the cell, plasmolysis that contracts a cell due to a loss of water through osmosis and peels the cell membrane off the cell wall, and so on.

In addition to natural cell lysis, various methods have been developed for performing cell lysis in a laboratory. Methods of cell lysis through physical disruption of cells include, for example, localized heating to cause protein denaturation, mechanical disruption using rotating blades to grind and disperse cells, liquid homogenization to force cells through a narrow space to shear cell membranes, sonication that uses high frequency sound waves to shear cells, repeated cycles of freezing and thawing to disrupt cells through ice crystal formation, and manual grinding of cell cultures frozen in liquid nitrogen. Methods of solution-based cell lysis include, for example, the use of hypotonic additives to decrease osmotic pressure to collapse the cell membrane, the use of hypertonic additives to increase osmotic pressure to burst the cell membrane, and the use of detergents. In many instances, the existing physical lysis methods are not scalable and cannot be used effectively in microfluidic lab-on-a-chip environments. For example, in some cases the solution-based methods can adversely dilute the sample, are slow in the lysing action, and are not selective in their application.

Accordingly, examples disclosed herein involve the use of a microfluidic device to enable cell lysis by exposing cells to high pressure spikes within an enclosed channel that break down cell membranes. A lysing element can include a thermal resistor disposed within a microfluidic channel to generate a vapor bubble. When the vapor bubble collapses, it can produce a high pressure spike within the channel that lyses a cell or cells within the localize area of the high pressure spike.

In a particular example, a method of cell lysis includes moving cell fluid from a first reservoir through a microfluidic channel toward a second reservoir. The method includes activating a lysing element multiple times as a cell from the cell fluid passes through the microfluidic channel. Activation of the lysing element is to lyse the cell. Lysate fluid resulting from the activation of the lysing element is then moved through the microfluidic channel into a second reservoir.

In another example, a microfluidic device for cell lysis includes a first reservoir to contain cell fluid and a second reservoir to contain lysate fluid. A fluid channel is in communication with the first reservoir and the second reservoir to move fluid from the first reservoir to the second reservoir. The device also includes a lysing element that is symmetrically located within the channel between the first and second reservoirs to lyse cells as the cell fluid moves from the first reservoir toward the second reservoir. In different examples, the channel includes a narrow channel section to increase pressure within the channel generated by the lysing element.

In another example, a method of cell lysis includes moving cell fluid from a first reservoir through an entry section of a channel and into a midsection of the channel. A first lysing device near the entry section of the channel and a second lysing device near an exit section of the channel can be activated at a first frequency to expose cells in the cell fluid to multiple pressure spikes to lyse the cells. The lysate fluid that results from the lysing can then be moved from the midsection of the channel through the exit section of the channel and into a second reservoir. In an implementation, fluid is moved through the channel by activating the first lysing device at a second frequency that is slower than the first frequency.

Figure 2:
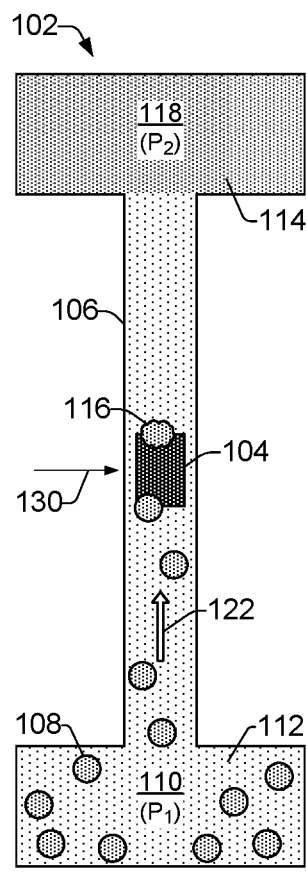
FIG. 2 shows an example of a microfluidic lysis device.

FIG. 1 shows an example of a microfluidic cell lysis system 100 that includes a microfluidic lysis device 102 for lysing cells. FIG. 2 shows an example of a microfluidic lysis device 102. Referring to FIGS. 1 and 2, the example lysis device 102 includes a lysing element 104 disposed within a microfluidic channel 106 to lyse cells 108. It is noted that examples of cells 108 are specifically illustrated in FIG. 2. However, for the sake of clarity, example cells 108 are not specifically illustrated in the illustrations of other example lysis devices 102 in subsequent FIGs. It is to be understood that the discussion of other example lysis devices 102 related to various FIGs. throughout this disclosure includes and/or presumes the presence of cells 108, even though such FIGs. may not specifically illustrate the cells 108.

As shown in FIGS. 1 and 2, the example cell lysis system 100 includes a first reservoir that can be referred to as an inlet reservoir 110, or cell fluid reservoir 110. The cell fluid reservoir 110 is to receive and temporarily store cell fluid 112, or fluidic cell culture 112. The cell fluid 112 can include various cells 108 of interest that are to be lysed, such as cells cultured from plants, animals, or bacteria suspended in an appropriate extracellular fluid medium such as interstitial fluid and blood plasma. For example, cell fluid 112 within the cell fluid reservoir 110 may comprise whole blood or components of blood including liquid plasma in which red and white blood cells are suspended. Lysate fluid 114 from the lysed cells 116 includes the intracellular components of the cells 108, and it is to be received and stored in a second reservoir that can be referred to as an outlet reservoir 118, or lysate fluid reservoir 118.

The cell fluid 112 within the cell fluid reservoir 110 can be received, for example, from an external cell fluid and pressure source 120 (FIG. 1). The cell fluid and pressure source 120 can provide the cell fluid 112, and in some examples it can also provide pressure to put the cell fluid 112 under pressure within the cell fluid reservoir 110. In some examples, the external cell fluid and pressure source 120 can generate a fluidic pressure differential between the cell fluid reservoir 110 and the lysate fluid reservoir 118 that causes fluid to flow through the channel 106 from the cell fluid reservoir 110 to the lysate fluid reservoir 118. As shown in FIG. 2, for example, the external source 120 may cause a fluidic pressure $P_1$ within the cell fluid reservoir 110 that results in a fluidic pressure $P_2$ within the lysate fluid reservoir 118, where the pressure $P_1$ is greater than the pressure $P_2$, resulting in a fluid flow from the cell fluid reservoir 110 to the lysate fluid reservoir 118, as indicated by direction arrow 122. An external cell fluid and pressure source 120 can be implemented, for example, as a syringe pump or a peristaltic pump fluidically coupled to the cell fluid reservoir 110.

A lysing element 104 can be implemented, for example, as a thermal bubble resistor element 104. Applying energy to the element 104 can super heat the element and the surrounding fluid, creating a vapor bubble within the channel 106. When the energy is removed from the element 104, the vapor bubble collapses. During the vapor bubble collapse, a fluidic bubble jet is produced that concentrates the residual kinetic energy of the bubble in a small area that provides extremely high pressure in the tip of the bubble jet. The high pressure spike from the collapsing bubble can be used to lyse cells 108 in a manner similar to that of an ultrasound agitator. The lysing element 104 can be activated at a frequency that ensures cell lysis by exposing passing cells to multiple high pressure spikes from multiple bubble collapse events.

As shown in FIG. 2, in some examples the lysing element 104 is symmetrically located within the channel 106 between the cell fluid reservoir 110 and the lysate fluid reservoir 118. That is, the lysing element 104 is located in the middle or at the center 130 of the channel which is an equal distance away from both the cell fluid reservoir 110 and the lysate fluid reservoir 118. The symmetric or central location of the lysing element 104 within the channel 106 enables activations of the lysing element 104 to lyse cells without the activations contributing to a net fluid flow within the channel.

Figure 3:
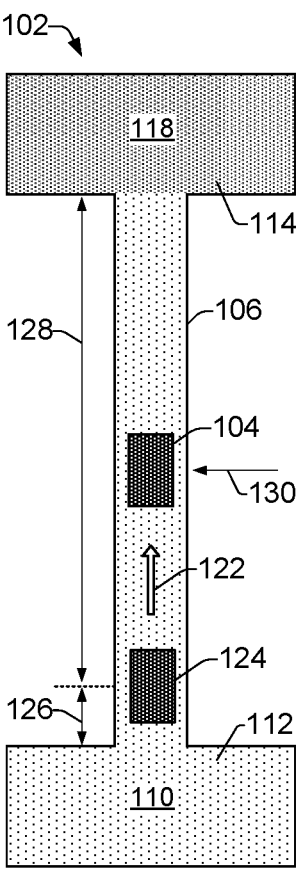
FIG. 3 shows an example of the microfluidic lysis device of FIG. 2 in which fluid flow through the channel is induced by an asymmetrically located pump element.

Fluid flow through the channel 106 in some examples, as noted above with regard to FIG. 2, can be induced by causing a pressure differential between the cell fluid reservoir 110 and the lysate fluid reservoir 118. In other examples, fluid flow through the channel 106 can be induced by operation of a pump element 124 that is asymmetrically located within the channel 106. FIG. 3 shows an example of the microfluidic lysis device 102 of FIG. 2 in which fluid flow through the channel 106 is induced by an asymmetrically located pump element 124, rather than by a pressure differential between the cell fluid reservoir 110 and the lysate fluid reservoir 118. The asymmetric placement of the pump element 124 within channel 106 creates a short side 126 (e.g., a short arm) of the channel 106 and a long side 128 (e.g., a long arm) of the channel 106. The asymmetric location of the pump 124 relative to the center 130 of the channel 106 in this manner creates inertial conditions that drive net fluid flow in a direction 122 toward the long side 128 of the channel 106. That is, the pump element 124 in the FIG. 3 example induces unidirectional fluid flow (i.e., fluid flow in one direction) within the channel 106 from the cell fluid reservoir 110 toward the lysate fluid reservoir 118 when the pump 124 is activated.

In some examples, a pump element 124 comprises a thermal bubble resistor element 124, like the lysing element 104. Thus, when activated, the pump element 124 generates a vapor bubble and creates a localized high pressure zone within the channel 106 adjacent the pump element 124 to produce a net fluid flow through the channel 106. While this mechanism is the same mechanism that can be used to lyse cells, as noted above, the frequency of activation of the pump element 124 can be controlled (i.e., reduced) to avoid exposing cells in the local vicinity of the pump element 124 to multiple pressure spikes that might prematurely lyse the cells. Therefore, based on its asymmetrical location within the channel 106 and its controlled frequency of operation, the pump element 124 can be managed to function as a fluid pumping mechanism that does not lyse cells. Conversely, based on its symmetrical location within the channel 106 and its higher frequency of operation, the lysing element 104 can be managed to function as a lysing mechanism and not a pumping mechanism.

Referring again to FIG. 1, an example microfluidic cell lysis system 100 includes a controller 132 to control the functionality of various system components to enable cell lysis in a microfluidic lysis device 102. In general, cell lysis within the example system 100 includes the movement of cell fluid 112 from the cell fluid reservoir 110 through the microfluidic channel 106 toward lysing element 104. Lysing element 104 functions to lyse cells 108 within the cell fluid 112 by exposing the cells 108 to multiple pressure spikes within the channel 106 as the cells pass within the localized area of the lysing element 104. Lysate fluid 114 from lysed cells 116 is then moved through the remainder of the channel 106 into the lysate reservoir 118.

As shown in FIG. 1, an example controller 132 can include a processor (CPU) 134 and a memory 136. The controller 132 may additionally include other electronics (not shown) for communicating with and controlling the various components of cell lysis system 100, such as discrete electronic components and an ASIC (application specific integrated circuit). Memory 136 can include both volatile (i.e., RAM) and nonvolatile memory components (e.g., ROM, hard disk, optical disc, CD-ROM, magnetic tape, flash memory, etc.). The components of memory 136 comprise non-transitory, machine-readable (e.g., computer/processor-readable) media that provide for the storage of machine-readable coded program instructions, data structures, program instruction modules, and other data and/or instructions executable by a processor 134 of the system 100.

An example of instructions stored in memory 136 include instructions associated with modules 138 and 140, while an example of stored data includes control data 142. In some examples, controller 132 can receive data 142 from a host system such as a computer. Data 142 represents, for example, data such as frequency, timing, and fluid pressure information associated with controlling the operation of system components such as lysing element 104, pump element 124, and the cell fluid-pressure source 120. Using control data 142, the processor 134 can execute instructions (e.g., from modules 138 and 140) to control components of system 100 to lyse cells from a cell fluid 112 to produce a lysate fluid 114. Modules 138 and 140 include programming instructions executable by processor 134 to cause the cell lysis system 100 to perform various functions related to moving fluid through channel 106, sensing cells 108 within the vicinity of lysing element 104, and activating lysing element 104, such as the operations of methods 1600, 1700, and 1800, described below with respect to FIGS. 16, 17, and 18, respectively.

In one example, instructions from the fluid pump-pressure module 140 are executable on processor 134 in different system implementations to control fluid moving mechanisms 144. As shown in FIG. 1, fluid moving mechanisms 144 can include the cell fluid-pressure source 120 and a pump element 124 within microfluidic channel 106. Thus, in some examples, instructions from the fluid pump-pressure module 140 are executable on processor 134 to control the cell fluid-pressure source 120 to provide cell fluid to the cell fluid reservoir 110, and to provide pressure to create a pressure differential between the cell fluid reservoir 110 and the lysate fluid reservoir 118 that induces fluid flow through the channel 106 in a direction 122. In other examples, instructions from module 140 are executable on processor 134 to control the timing and frequency of operation for a pump element 124 to induce fluid flow within the channel 106 in a direction 122 from the cell fluid reservoir 110 to the lysate fluid reservoir 118.

In another example, instructions from the cell lysing-sensing module 138 are executable on processor 134 to control the timing and frequency of activation of the lysing element 104. In some examples, the timing of activation of the lysing element 104 can be controlled passively using timing data from control data 142. In other examples, the timing of activation of the lysing element 104 can be controlled actively using sensory information received from a cell sensing element.

Figure 4:
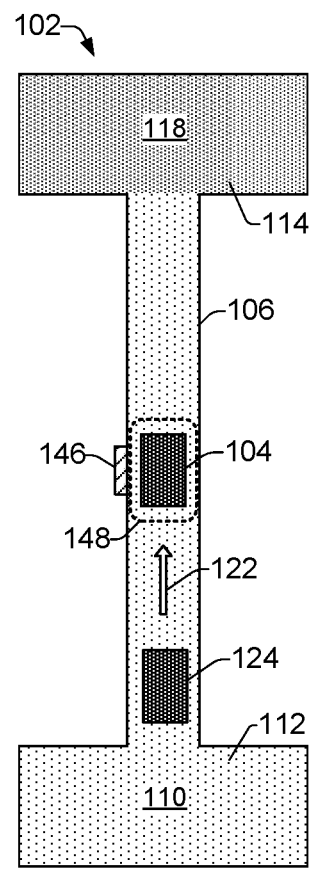
FIG. 4 shows an example of the microfluidic lysis device of FIG. 2 in which a cell sensing element is disposed within the microfluidic channel.

FIG. 4 shows an example of the microfluidic lysis device 102 of FIG. 2 in which a cell sensing element 146 is disposed within or around the microfluidic channel 106 in the vicinity 148 of the lysing element 104. The cell sensing element 146 is to sense when a cell 108 is within a lysing proximity 148 of the lysing element 104, and to provide the sensory information to the processor 134, which in turn can activate the lysing element 104 based on a sensed presence of a cell 108. In this manner, the lysis device 102 in system 100 enables lysis-on-demand through controlling the timing of activation of the lysing element 104 rather than having the lysing element 104 run in a continual activation mode. A cell sensing element 146 can include, for example, an optical sensor that can sense the contours of cells 108 by refraction and/or reflection of the cell membrane as cells pass within the vicinity or lysing proximity 148 of the lysing element 104, or an impedance sensor that includes electrodes to sense changes in impedance across the channel 106 as cells 108 pass between the electrodes. A lysing proximity 148 can vary depending on the type of cell being lysed. In some examples, a lysing proximity 148 can encompass a border area immediately around the lysing element 104. In some examples, the lysing proximity 148 can include a border area that extends somewhat farther on either side of the lysing element 104. In some examples, the lysing proximity 148 can include an area near the lysing element 104 in which a cell 108 is passing at least partially over the lysing element 104.

FIGS. 5 through 15b show different examples of a microfluidic lysis device 102 in varying configurations that can include different fluid moving mechanisms 144 (FIG. 1), as well as different channel width features to amplify pressure spikes generated by collapsing vapor bubbles from lysing elements 104. Referring generally to FIGS. 5 through 9, for example, each of the lysis devices 102 illustrates a pressure differential of $P_1$ to $P_2$ from the cell fluid reservoirs 110 to the lysate fluid reservoirs 118. The illustrated pressure differentials, along with the lack of any pump elements shown in the devices 102 in FIGS. 5 through 9, indicates that the fluid moving mechanism 144 (FIG. 1) being implemented in each of the lysis devices 102 shown in FIGS. 5 through 9 is an external pressure source 120, as shown in FIG. 1. By contrast, referring generally to FIGS. 10 through 15b (i.e., FIGS. 10, 11, 12, 13, 14, 15a and 15b), the fluid moving mechanism 144 in each of the lysis devices 102 comprises a pump element 124, as illustrated.

Figure 5:
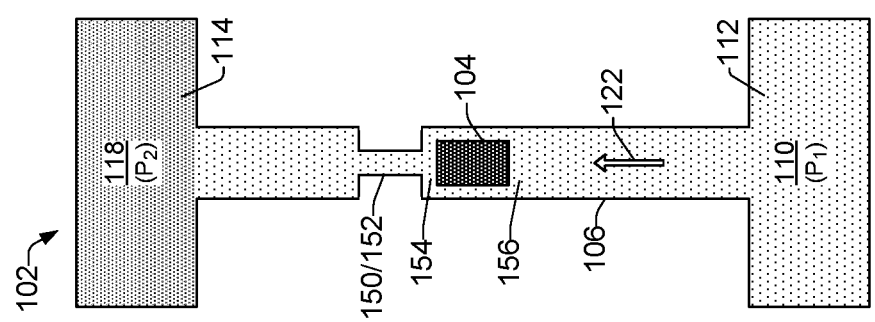

Referring to FIG. 5, the example lysis device 102 includes a pressure differential of $P_1$ to $P_2$ from the cell fluid reservoir 110 to the lysate fluid reservoir 118 to induce fluid flow in direction 122. Like the example lysis device of FIG. 2 discussed above, a lysing element 104 is symmetrically located between the cell fluid reservoir 110 and the lysate fluid reservoir 118, at the midpoint or center 130 of the channel 106 to enable the lysing element 104 to lyse cells without contributing a net fluid flow within the channel. In the example device 102 of FIG. 5, the channel 106 includes a narrow channel section 150 between the lysing element 104 and the lysate fluid reservoir 118. Thus, the channel 106 can be said to have a first width, while the narrow channel section 150 has a second width that is narrower than the first width. In this example, the narrow channel section 150 can be referred to as a pinch point 152 because the narrow channel section 150 remains narrow for just a small portion of the channel length.

A narrow channel section 150, such as a pinch point 152, increases the pressure within the narrow section induced by a collapsing bubble generated by lysing element 104. The increased pressure within the narrow channel section 150 provides for faster and more efficient lysing of cells 108 as they pass through the narrow channel section 150 and are exposed to pressure spikes from collapsing vapor bubbles. In general, narrower channels on one side of the lysing element 104, such as at the exit area 154 of the lysing element 104, can modify the bubble collapse and increase the bubble pressure. Thus, narrowing the width of the channel 106, as shown by the narrow channel section 150 in the FIG. 5 example and in subsequent examples, results in higher pressure within the channel without increasing the size of the lysing element 104. The exit area 154 of the lysing element 104 generally comprises the channel area just after the lysing element 104 as fluid flows in the direction 122 toward the lysate fluid reservoir 118. An entry area 156 of the lysing element 104 comprises the channel area just prior to the lysing element 104 as fluid flows in the direction 122 from the cell fluid reservoir 110 toward the lysate fluid reservoir 118.

Figure 8:
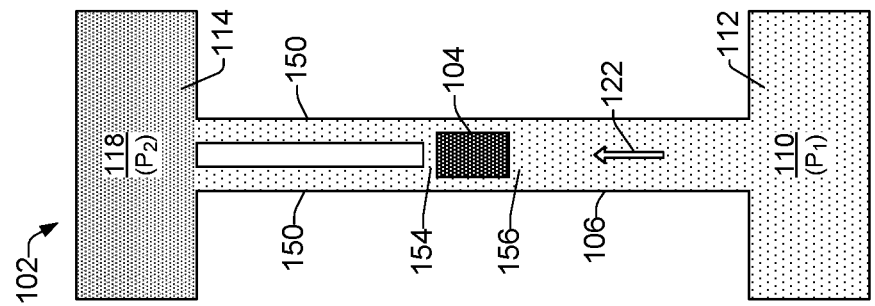
FIGS. 5, 6, 7, 8, and 9, show examples of microfluidic lysis devices that each have a fluid moving mechanism comprising a pressure differential between a cell fluid reservoir and a lysate fluid reservoir.
Figure 7:
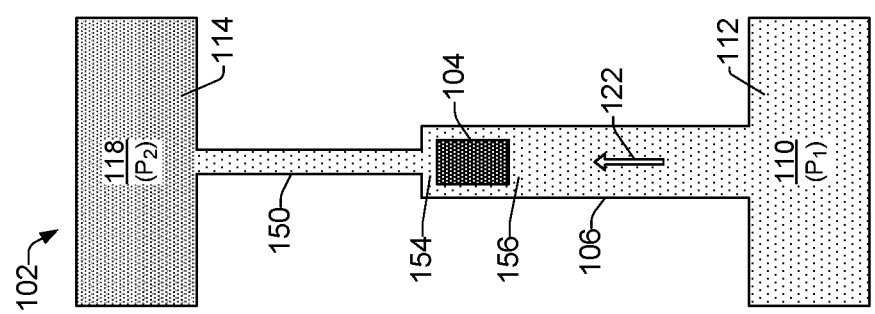
Figure 6:
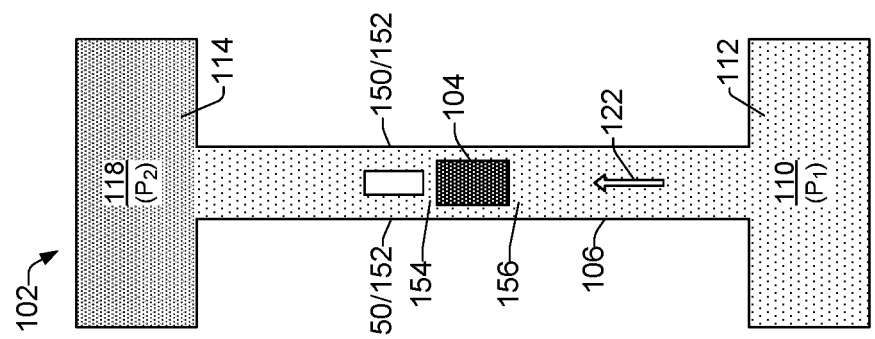

Referring to FIGS. 6, 7, and 8, example lysis devices 102 each include a pressure differential of $P_1$ to $P_2$ from the cell fluid reservoir 110 to the lysate fluid reservoir 118 to induce fluid flow in direction 122, and a lysing element 104 symmetrically located between the cell fluid reservoir 110 and the lysate fluid reservoir 118 to enable cell lysis while not contributing to a net fluid flow within the channel 106. In the example device 102 of FIG. 6, the channel 106 includes multiple (e.g., two) narrow channel sections 150 implemented as pinch points 152 positioned at the exit area 154 of the lysing element 104, between the lysing element 104 and the lysate fluid reservoir 118. Thus, the channel 106 can be said to have a first width, while the narrow channel sections 150/152 have a second width that is narrower than the first width. In the example device 102 of FIG. 7, the channel 106 includes a narrow channel section 150 that begins at the exit area 154 of the lysing element 104 and extends to the lysate fluid reservoir 118. Thus, the narrow channel section 150 in the FIG. 7 example is longer than a pinch point. In the example device 102 of FIG. 8, the channel 106 includes multiple (e.g., two) narrow channel sections 150 that begin at the exit area 154 of the lysing element 104 and extend to the lysate fluid reservoir 118. Thus, the narrow channel sections 150 in the FIG. 8 example are longer than pinch points.

Figure 9:
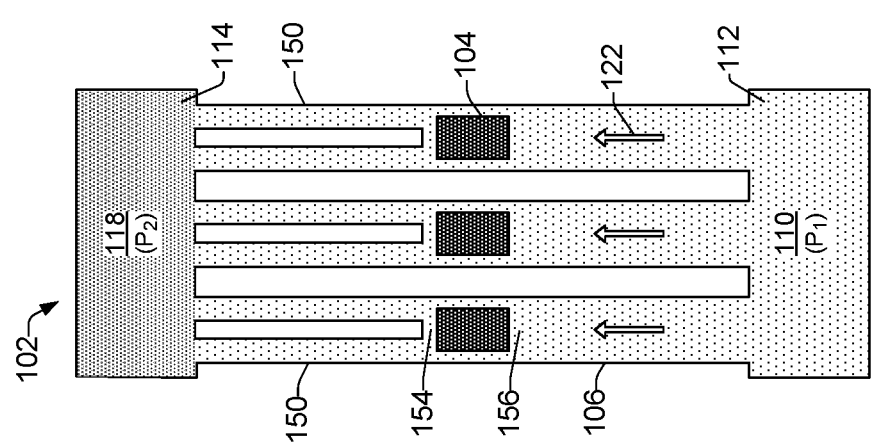

Referring now to FIG. 9, an example lysis device 102 includes multiple (e.g., three) microfluidic channels 106 communicating between the cell fluid reservoir 110 and the lysate fluid reservoir 18. Similar to the previous examples in FIGS. 5 through 8, the example device 102 of FIG. 9 includes a pressure differential of $P_1$ to $P_2$ from the cell fluid reservoir 110 to the lysate fluid reservoir 118 to induce fluid flow in the direction 122. Located symmetrically within each channel 106, is a lysing element 104 to enable cell lysis within each channel while not contributing to a net fluid flow through the channels 106. Similar to the example in FIG. 8, each of the multiple channels 106 includes multiple (e.g., two) narrow channel sections 150 that begin at the exit areas 154 of respective lysing elements 104 and extend to the lysate fluid reservoir 118.

As noted above, example lysis devices 102 shown in FIGS. 10 through 15b, each comprises a pump element 124 as fluid moving mechanisms 144 to induce fluid flow in a direction 122 from a cell fluid reservoir 110 toward a lysate fluid reservoir 118. Pump elements 124 implemented as thermal bubble resistor elements can be operated at a frequency sufficient to induce fluid flow within the channel 106, while not exposing cells 108 from the cell fluid reservoir 110 to multiple pressure spikes that might lyse the cells. By contrast, lysing elements 104 implemented as thermal bubble resistor elements can be operated at a higher frequency than the pump elements 124 in order to expose the cells to multiple high pressure spikes resulting in lysing of the cells.

Figure 11:
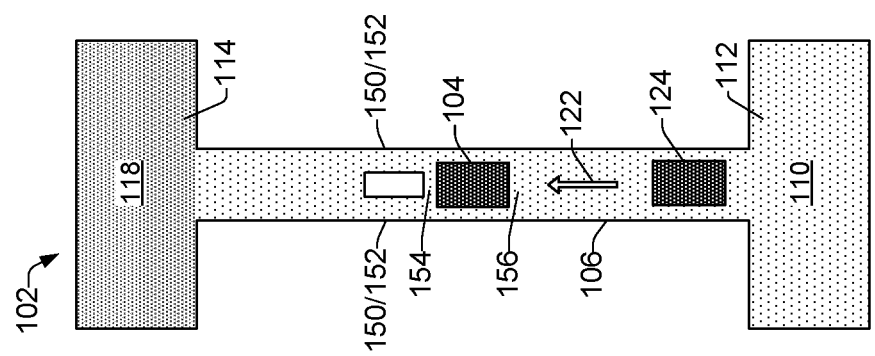
Figure 10:
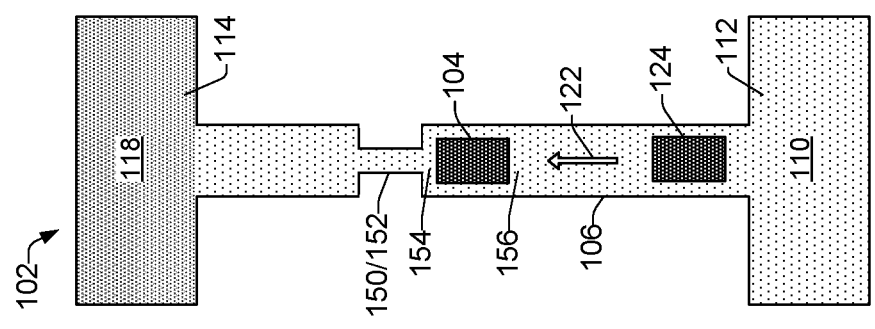

In the example lysis devices 102 of FIGS. 10 and 11, other than the pump elements 124 as fluid moving mechanisms 144, the devices are arranged in the same manner as respective lysis devices 102 of FIGS. 5 and 6, discussed above. Thus, example device 102 of FIG. 10 includes a lysing element 104 symmetrically located between the cell fluid reservoir 110 and the lysate fluid reservoir 118, and a narrow channel section 150 or pinch point 152 between the lysing element 104 and the lysate fluid reservoir 118 to provide more effective cell lysing through increased pressure on cells moving through the pinch point 152. Similar to the lysis device 102 of FIG. 6, the microfluidic channel 106 of device 102 of FIG. 11 includes multiple (e.g., two) narrow channel sections 150 implemented as pinch points 152. The pinch points 152 are positioned at the exit area 154 of the lysing element 104, between the lysing element 104 and the lysate fluid reservoir 118. Thus, the channel 106 can be said to have a first width, while the narrow channel sections 150/152 have a second width that is narrower than the first width.

Figure 12:
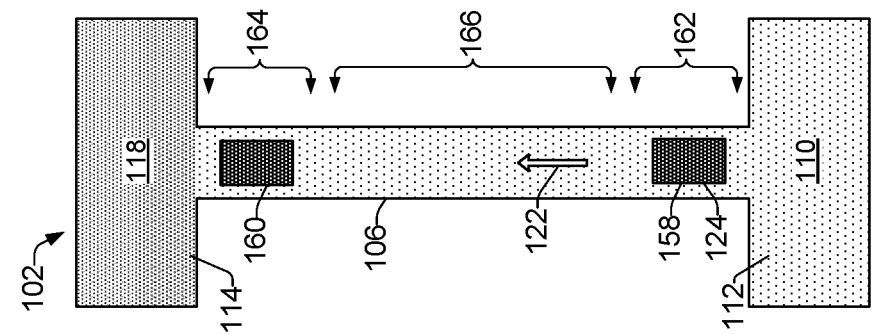

Referring now to FIGS. 12 through 14, in some examples, a lysis device 102 can include lysing elements that operate in a dual role as both lysing elements and as pump elements. In FIG. 12, lysing elements 158 and 160 are positioned, respectively, in a channel entry section 162 and in a channel exit section 164. Lysing element 158 can be operated at a frequency that moves cell fluid 112 in a direction 122 from the cell fluid reservoir 110 through the channel entry section 162 and into a channel midsection 166. In this respect, lysing element 158 becomes a dual role element and operates as a pump element 124. Both lysing elements 158 and 160 can then be operated at a higher frequency to expose cell within the cell fluid 112 to multiple high pressure spikes that cause lysing of the cells. Lysing element 158 can then be operated again at a lower frequency as a pump element 124 to move the resulting lysate fluid from the channel midsection 166, through the channel exit section 164 and into the lysate fluid reservoir 118.

Example lysis devices 102 shown in FIGS. 13 and 14 operate in a manner similar to the lysis device 102 of FIG. 12. However, the example lysis devices 102 of FIGS. 13 and 14 additionally include narrow channel sections 150 and/or pinch points 152 to provide more effective cell lysing through increased pressure on cells as they move through the channel 106. In the lysis device 102 of FIG. 13, for example, there is a narrow channel section 150 extending along the channel midsection 166 between the two lysing elements 158 and 160, and a pinch point 152 positioned in the channel 106 between the lysing element 160 and the lysate fluid reservoir 118. In the example lysis device 102 of FIG. 14, there is a pinch point 152 extending along a short portion of the channel midsection 166 between the two lysing elements 158 and 160, and a pinch point 152 positioned in the channel 106 between the lysing element 160 and the lysate fluid reservoir 118.

Referring to FIGS. 15a and 15b, example lysing devices 102 comprise alternate implementations of the lysing device 102 described above with regard to FIG. 4. The example lysing devices 102 of FIGS. 15a and 15b each include a cell sensing element 146 disposed within or around the microfluidic channel 106 in the vicinity 148 of the lysing element 104. As noted above, a cell sensing element 146 enables lysis-on-demand by sensing when a cell 108 is within a lysing proximity 148 of the lysing element 104, and providing the sensory information to the processor 134, which in turn can activate the lysing element 104 based on a sensed presence of a cell 108. In addition to having a cell sensing element 146, the example lysing devices 102 in FIGS. 15a and 15b include multiple (e.g., two) narrow channel sections 150 that begin at the exit area 154 of the lysing element 104 and extend to the lysate fluid reservoir 118. These narrow channel sections 150 function as discussed above with regard to FIG. 8. The example lysing devices 102 shown in FIGS. 15a and 15b additionally comprise pump elements 124 that are located within auxiliary microfluidic channels 168 that intersect the main microfluidic channel 106. The auxiliary microfluidic channels 168 and pump elements 124 are asymmetrically located along the main channel 106 with respect to the cell fluid reservoir 110 and lysate fluid reservoir 118 in order to induce fluid flow in the direction 122 from the cell fluid reservoir 110 toward the lysate fluid reservoir 118. The auxiliary channel 168 in FIG. 15a intersects the main microfluidic channel 106 at one end and the cell fluid reservoir 110 at another end, while the auxiliary channel 168 in FIG. 15b is a straight channel that intersects the main channel 106 at one location. It is noted that other examples of auxiliary channels with pump elements are also contemplated, such as auxiliary channels that intersect the main channel 106 at an angle and auxiliary channels that form a loop off the main channel 106, intersecting the main channel 106 at two locations.

Figure 16:
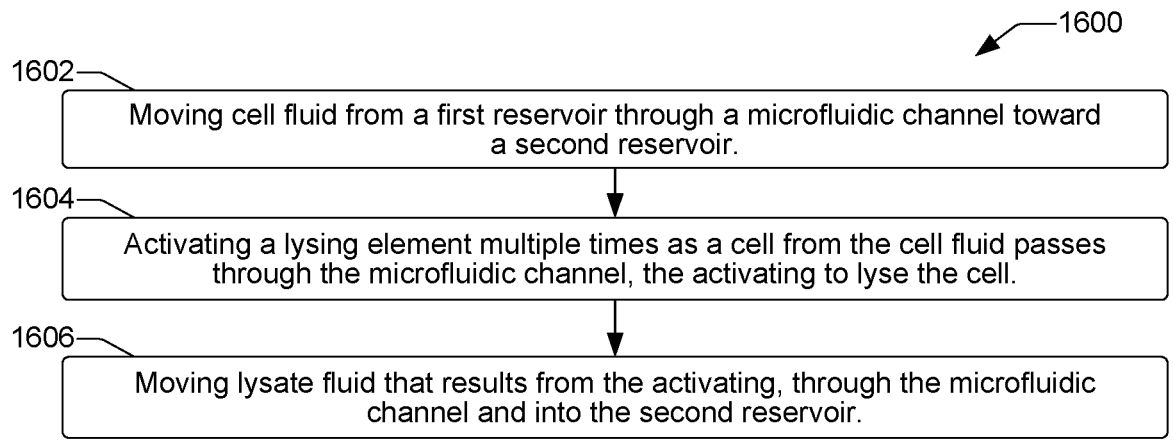
FIGS. 16, 17, and 18, are flow diagrams that show example methods of cell lysis in a microfluidic cell lysis device.
Figure 18:
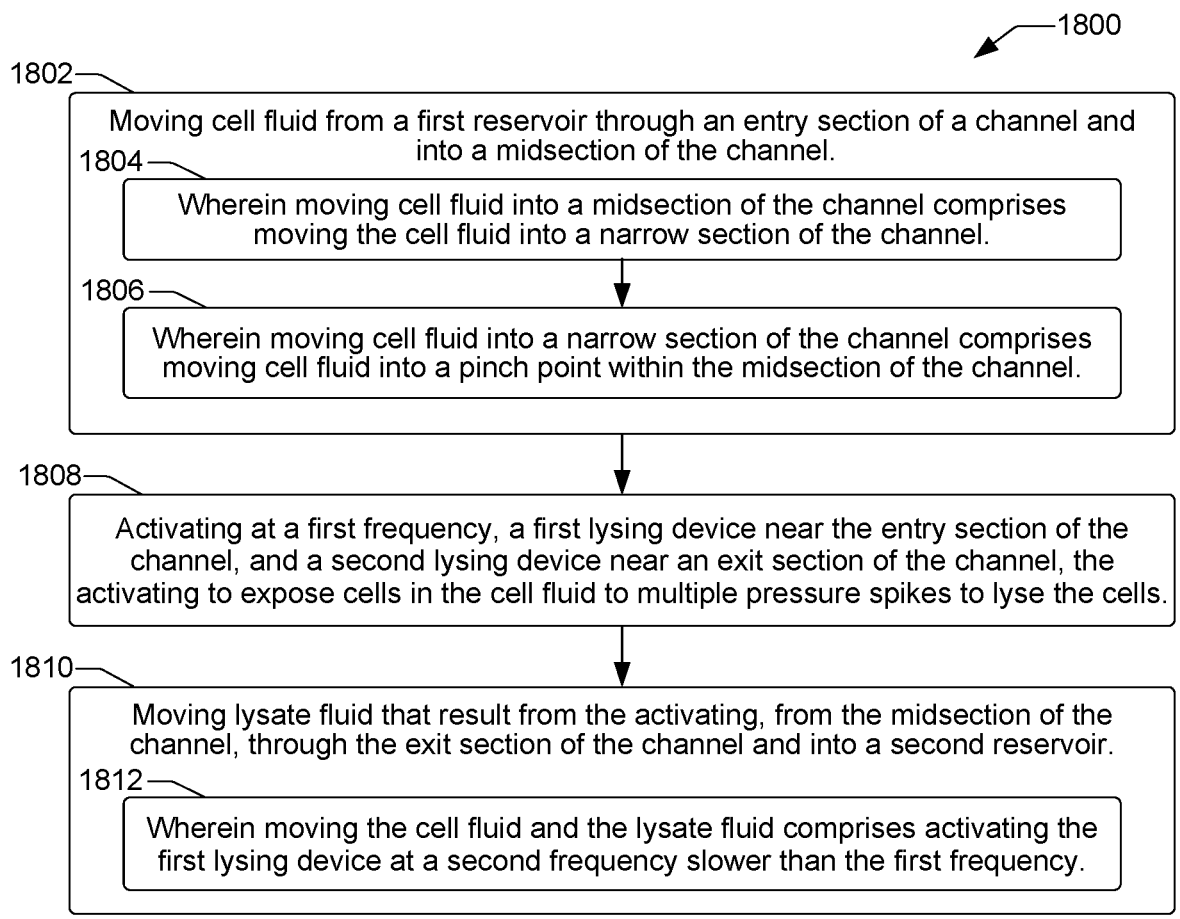
Figure 17:
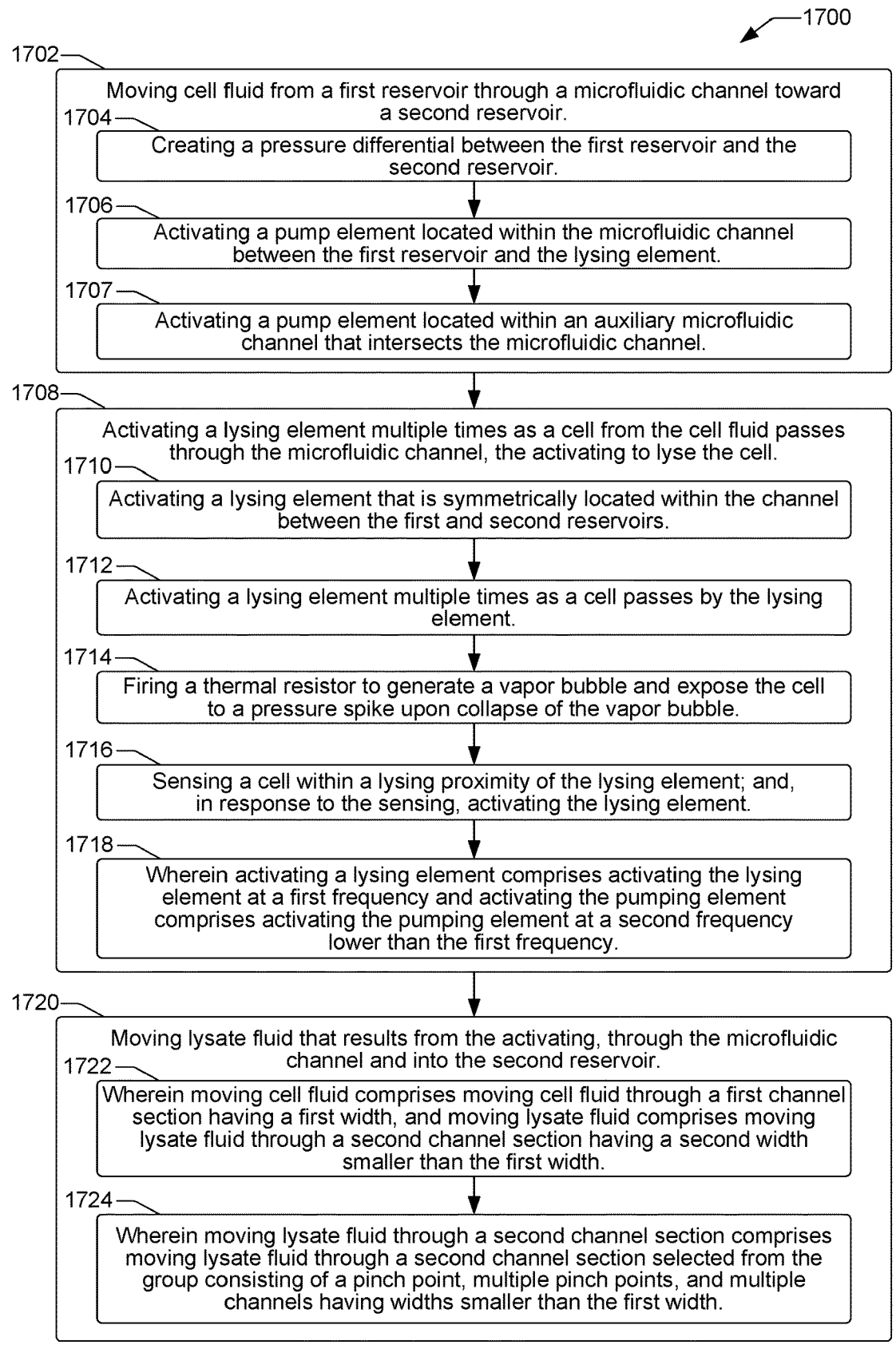

FIGS. 16, 17, and 18 are flow diagrams showing example methods 1600, 1700, and 1800 of cell lysis in a microfluidic cell lysis device such as the example cell lysis devices 102 discussed above with regard to FIGS. 1 through 15. Method 1700 is an extension of method 1600 that incorporates additional details of a cell lysis method. The methods can be performed in a microfluidic cell lysis device under the control of a controller having a processor to execute control instructions such as controller 132 shown in FIG. 1.

Referring now to method 1600 of FIG. 16, an example method of cell lysis includes moving cell fluid from a first reservoir through a microfluidic channel toward a second reservoir, as shown at block 1602. As shown at block 1604, the method includes activating a lysing element multiple times as a cell from the cell fluid passes through the microfluidic channel. Activating the lysing element multiple times exposes the cell to multiple pressure spikes to lyse the cell. The method then includes moving the lysate fluid that results from the activating through the microfluidic channel and into the second reservoir, as shown at block 1606.

Referring now to FIG. 17, an example method 1700 of cell lysis is provided that incorporates additional details of the cell lysis method 1600 of FIG. 16. Thus, the example method 1700 includes moving cell fluid from a first reservoir through a microfluidic channel toward a second reservoir, as shown at block 1702. In some examples, moving cell fluid from a first reservoir through a microfluidic channel toward a second reservoir can include creating a pressure differential between the first reservoir and the second reservoir, as shown at block 1704. In some examples, moving cell fluid from a first reservoir through a microfluidic channel toward a second reservoir can include activating a pump element located within the microfluidic channel between the first reservoir and the lysing element, as shown at block 1706. In some examples, moving cell fluid from a first reservoir through a microfluidic channel toward a second reservoir can include activating a pump element located within an auxiliary microfluidic channel that intersects the microfluidic channel, as shown at block 1707.

The method 1700 can continue as shown at block 1708, with activating a lysing element multiple times as a cell from the cell fluid passes through the microfluidic channel. Activating the lysing element multiple times exposes the cell to multiple pressure spikes to lyse the cell. In some examples, activating a lysing element can include activating a lysing element that is symmetrically located within the channel between the first and second reservoirs, as shown at block 1710. In some examples, activating a lysing element can include activating a lysing element multiple times as a cell passes by the lysing element, as shown at block 1712. In some examples, activating a lysing element can include firing a thermal resistor to generate a vapor bubble and expose the cell to a pressure spike upon collapse of the vapor bubble, as shown at bock 1714. In some examples, as shown at block 1716, activating a lysing element can include sensing a cell within a lysing proximity of the lysing element, and, in response to the sensing, activating the lysing element. In some examples, as shown at block 1718, activating a lysing element can include activating the lysing element at a first frequency and activating the pump element (block 1706) can include activating the pump element at a second frequency lower than the first frequency.

The method 1700 can continue as shown at block 1720, with moving the lysate fluid that results from the activating through the microfluidic channel and into the second reservoir. In some examples, as shown at block 1722, moving cell fluid (block 1702) can include moving cell fluid through a first channel section having a first width, and moving lysate fluid can include moving lysate fluid through a second channel section having a second width smaller than the first width. In some examples, as shown at block 1724, moving lysate fluid through a second channel section can include moving lysate fluid through a second channel section, where the second channel section is a section selected from the group consisting of a pinch point, multiple pinch points, and multiple channels having widths smaller than the first width.

Referring now to FIG. 18, an example method 1800 of cell lysis includes moving cell fluid from a first reservoir through an entry section of a channel and into a midsection of the channel, as shown at block 1802. In some examples, as shown at block 1804, moving cell fluid from a first reservoir through an entry section of a channel and into a midsection of the channel can include moving the cell fluid into a narrow section of the channel. In some examples, moving cell fluid into a narrow section of the channel can include moving cell fluid into a pinch point within the midsection of the channel, as shown at block 1806.

As shown at block 1808, the method 1800 includes activating at a first frequency, a first lysing device near the entry section of the channel and a second lysing device near an exit section of the channel. Activating the first and second lysing devices is to expose cells in the cell fluid to multiple pressure spikes in order to lyse the cells. The method can then continue with moving lysate fluid that results from the activating, from the midsection of the channel, through the exit section of the channel and into a second reservoir, as shown at block 1810. In some examples, as shown at block 1812, moving the cell fluid and the lysate fluid comprises activating the first lysing device at a second frequency slower than the first frequency.

What is claimed is:

1. A microfluidic device for cell lysis comprising:
    a first reservoir to contain cell fluid;
    a second reservoir to contain lysate fluid;
    a single, nonintersecting fluid channel extending between and in communication with the first reservoir and the second reservoir to move cell fluid from the first reservoir toward the second reservoir; and,
    a lysing element symmetrically located within the nonintersecting fluid channel between the first and second reservoirs to lyse cells as the cell fluid moves from the first reservoir toward the second reservoir.

2. A microfluidic device as in claim 1, wherein the nonintersecting fluid channel comprises a narrow channel section between the lysing element and the second reservoir to increase pressure within the nonintersecting fluid channel generated by the lysing element.

3. A microfluidic device as in claim 1, wherein the nonintersecting fluid channel comprises multiple nonintersecting fluid channels and the lysing element comprises multiple lysing elements, one lysing element symmetrically located within each of the multiple nonintersecting fluid channels.

4. A microfluidic device as in claim 1, wherein the nonintersecting fluid channel comprises an intersecting fluid channel, the device further comprising:
- an auxiliary fluid channel that intersects the intersecting fluid channel at an asymmetric location that is closer to the first reservoir and farther from the second reservoir; and,
- a pump element within the auxiliary fluid channel to induce cell fluid to flow from the first reservoir toward the second reservoir.

5. A microfluidic device as in claim 1, further comprising a sensing element associated with the nonintersecting fluid channel to sense cells within a lysing proximity of the lysing element, and to initiate activation of the lysing element based on sensing the cells.

6. A microfluidic device as in claim 1, wherein the lysing element comprises a resistor element to generate vapor bubbles and expose cells to high pressure upon collapse of the vapor bubbles.

7. A microfluidic device as in claim 2, wherein the narrow channel section comprises a pinch point.

8. A microfluidic device as in claim 2, wherein the narrow channel section comprises multiple narrow channel sections.

9. A microfluidic device as in claim 1, further comprising a pressure source to create a pressure differential between the first and second reservoirs to induce cell fluid to flow from the first reservoir to the second reservoir.

10. A microfluidic device as in claim 1, further comprising a pump element within the fluid channel between the lysing element and the first reservoir to induce cell fluid to flow from the first reservoir to the second reservoir.

11. A microfluidic device as in claim 4, wherein a first end of the auxiliary fluid channel intersects the intersecting fluid channel, and a second end of the auxiliary fluid channel is closed.

12. A microfluidic device as in claim 4, wherein a first end of the auxiliary fluid channel intersects the intersecting fluid channel, and a second end of the auxiliary fluid channel intersects the first reservoir.

* * * * *